United States Patent [19]

Peikin

[11] Patent Number: 4,491,578

[45] Date of Patent: Jan. 1, 1985

[54] METHOD OF STIMULATING SATIETY IN MAMMALS

[76] Inventor: Steven R. Peikin, 510 Lombard St., Philadelphia, Pa. 19147

[21] Appl. No.: 516,937

[22] Filed: Jul. 25, 1983

Related U.S. Application Data

[63] Continuation-in-part of Ser. No. 388,088, Jun. 14, 1982, abandoned.

[51] Int. Cl.³ ............... A61K 37/00; A61K 31/27; A61K 31/24
[52] U.S. Cl. .................... 424/177; 424/300; 424/309
[58] Field of Search ............ 424/309, 177, 300

[56] References Cited

U.S. PATENT DOCUMENTS 4,073,884  2/1978  Hartdegen et al. ............... 424/94

OTHER PUBLICATIONS

Chem. Abst. 84, 133(e), (1976)–Okegawa et al.
Chem. Abst. 84, 218(m), (1976)–Aishita et al.
Chem. Abst. 99, 16995(h), (1983)–McLaughlin et al.

*Primary Examiner*—Douglas W. Robinson

[57] ABSTRACT

This disclosure relates to a method of eliciting satiety (psycho phenomenetic sense of being filled) in mammals through the administration of an effective amount of a trypsin inhibitor and is based on the postulate that the enzyme trypsin, normally secreted by the pancreas, constitutes a negative feedback signal for cholecystokinin secretion which in turn comprises a putative satiety signal; thus, the effect of the trypsin inhibitor is to increase the concentration of cholecystokinin secretion advancing the sensation of satiety resulting in a consequent decrease in food intake and, over time, body weight.

2 Claims, No Drawings

METHOD OF STIMULATING SATIETY IN MAMMALS

BACKGROUND OF THE INVENTION

This is a continuation in part of Application Ser. No. 06/388,088 filed June 14, 1982, now abandoned.

It has long been held that the trypsin inhibitor naturally present in raw soybean meal has a negative food efficiency characteristic and is accountable for the reduced rate of growth in animals placed on such feed, although this has never been proven. Thus, feeding of a raw soybean diet to rats has resulted in an enlarged pancreas as well as a decrease in the rate of body weight gain. On the basis of the foregoing, it was hypothosized that the efficiency of the food intake was adversely affected by reason of the presence of the trypsin inhibitor in the raw soybean meal. The negative food efficiency characteristic has been avoided by cooking the soybean meal before it is fed to animals.

It has been determined by reason of the present invention that the quantity of food intake by a mammal (including humans) may be reduced by orally ingesting a quantity of a synthetic trypsin inhibitor. It is hypothesized that the trypsin inhibitor induces the release of a satiety peptide comprising endogenous cholecystokinin (hereinafter CCK) which in turn acts as a putative feedback signal having the effect of decreasing food intake and, over time, body weight.

This hypothesis is supported by the results of several experiments. Pancreatic secretion, influenced in large part by CCK, has been shown to increase upon infusion of soybean trypsin inhibitors in the proximal one-third of the small intestine, which contains most of the CCK present in the gastrointestinal mucosa, and was decreased by infusion of trypsin in the same area. Amylase secretion from the perfused pancreas has also been shown to increase when serum from rats fed a diet with a trypsin inhibitor was compared with serum from rats fed the same diet without the trypsin inhibitor. Gastric administration of soybean trypsin inhibitors to rats is known to decrease the content of CCK in the upper duodenum within 20 minutes. Finally, chronic administration of CCK-peptides (CCK-33, CCK-8 and caerulein) has been known to simulate the effect of trypsin inhibitors by causing increased pancreas weight and DNA and protein content.

Decreased body weight gain in rats fed raw soybeans may also result from increased endogenous secretion of CCK induced by trypsin inhibitors present therein. It is reasonable to conclude that CCK serves as a satiety peptide in the control of food intake since exogenous administration of CCK has been shown to decrease food intake. Thus, increased CCK released soybean trypsin inhibitors may decrease food intake and, over time, may decrease body weight. The term "satiety" and variations thereof as used in explanation of the present invention is consistent with commonly accepted terminology, exemplary of which are the definitions set forth in Webster's New Collegiate Dictionary, Second Edition which defines satiety as the state of being satiated; and satiate as being full to satiety. Funk and Wagnellis Encyclopedic College Dictionary states that to satiate means to satisfy the appetite or desire of.

SUMMARY OF THE INVENTION

Trypsin inhibitors are commercially available from various pharmaceutical suppliers; however, heretofore they have been administered parenterally in the treatment of pancreatitis, symptomatic of which is the escape of proteolytic enzymes from the intestinal tract. I have found that the administration of therapeutically effective quantities of commercially available trypsin inhibitors in Zucker rats, under controlled conditions, resulted in a decreased daily food intake in both obese and lean rats without adverse side effects. Tests, conducted on both a daily basis and over an extended period of time, substantiate the conclusion that by administering controlled quantities of trypsin inhibitors to mammals will result in the elicitation to satiety within the mammal as a consequence of which the average per-meal food intake will decrease as will body weight.

Accordingly, the primary objective of the present invention is to set forth a method for eliciting satiety in mammals through the administration of therapeutically effective quantities of a trypsin inhibitor as a consequence of which negative feedback signals otherwise available from trypsin secreted from the pancreas is unavailable to check the secretion of CCK resulting in an early termination of food intake and, over time, a decrease in body weight.

DESCRIPTION OF THE INVENTION

Experiments were conducted to measure the feeding behavior responses of rats to a single administration of a trypsin inhibitor (hereinafter TI); and, the food intake and body weight responses to 7-day administration of TI. Zucker obese rats were used because they have previously been shown to be less sensitive to the effects of CCK on satiety and to the effects of CCK and TI on pancreas growth. As a result of these experiments, it has been shown that TI, administered as a single dose, decreased daily food intake by decreasing average meal size on both obese and lean rats; and, administered for 7 days, decreased food intake and body weight only in obese rats.

Experiment I. Feeding Behavior Response to TI

Five obese and five lean (552± vs. 399±16 g) male Zucker rats were individually housed in plexiglas operant chambers (Lafayette Instrument Company, Lafayette, Ind.) in a room maintained at constant temperature (24° C.) and 12-hour light-dark cycle.

For four weeks before initiation of the experiment rats were trained, using a continuous reinforcement schedule to press a bar to obtain food pellets (P. J. Noyes Company). During the same time they were adapted to a schedule of being fasted for 5.75 hours (beginning at "lights on"), being dosed intragastrically with 2.0 ml/kg water and, 15 minutes later, given access to the bar to press for food. During the treatment period rats were administered control or TI (N, N-dimethylcarbamoyl 4-[4-guanidino-benzoyloxy]-penyl acetate methane sulfate, obtained from Ono Pharmaceutical Co., Ltd., Osaka, Japan) using cross over designs to assign treatments. On experimental Day 1, half the obese and lean pairs of rats were administered 50 mg/kg TI and the other half were administered control treatments (saline solution) and feeding behavior was recorded for 18 hours. On experimental Day 2, 48 hours later, the treatments were reversed for each rat. On subsequent experimental days the sequence of doses tested was 25, 200, and 100 mg/kg TI. In addition, ad libitum fed rats were administered 200 mg/kg TI to determine the influence of the pretreatment fast on responses measured.

Feeding behavior patterns were analyzed using an automated data collection system. Each bar press for food was recorded on a Kennedy 9-track 800 bit per inch magnetic tape using a Massey-Dickinson data collection system to encode data with a time base. Data on the magnetic tape were sorted, stored and analyzed by a Varian 620/F100 computer. Meal patterns were determined using the criteria of at least 10 presses in 10 minutes with a minimum of 10 minute intermeal intervals. Feeding behaviors were analyzed for significant treatment effects using paired-t tests. The results of these tests are recorded in Table I which follows.

TABLE I

First and second meal feeding behavior response to oral administration of trypsin inhibitor in Zucker obese and lean rats.

| | Obese | | Lean | |
| --- | --- | --- | --- | --- |
| | 0 | TI | 0 | TI |
| First meal, number presses | | | | |
| 25 mg/kg, 6 hr. fasted | 103 ± 6 | 100 ± 2 | 70 ± 18 | 73 ± 20 |
| 50 mg/kg, 6 hr. fasted | 100 ± 6 | 97 ± 14 | 60 ± 9 | 61 ± 16 |
| 100 mg/kg, 6 hr. fasted | 137 ± 7 | 108 ± 12* | 113 ± 24 | 119 ± 25 |
| 200 mg/kg, 6 hr. fasted | 118 ± 28 | 80 ± 25 | 87 ± 17 | 27 ± 9 |
| 200 mg/kg, ad lib fed | 27 ± 3 | 60 ± 6** | 36 ± 13 | 26 ± 4 |
| Postmeal interval, min | | | | |
| 25 mg/kg, 6 hr. fasted | 205 ± 33 | 168 ± 31 | 208 ± 24 | 230 ± 33 |
| 50 mg/kg, 6 hr. fasted | 216 ± 30 | 103 ± 14** | 204 ± 20 | 196 ± 34 |
| 100 mg/kg, 6 hr. fasted | 228 ± 28 | 124 ± 17** | 280 ± 41 | 177 ± 25** |
| 200 mg/kg, 6 hr. fasted | 233 ± 23 | 127 ± 15** | 233 ± 23 | 167 ± 24* |
| 200 mg/kg, ad lib fed | 225 ± 34 | 174 ± 16 | 102 ± 32 | 134 ± 21 |
| Second meal, number presses | | | | |
| 25 mg/kg, 6 hr. fasted | 36 ± 10 | 42 ± 11 | 32 ± 10 | 34 ± 10 |
| 50 mg/kg, 6 hr. fasted | 51 ± 3 | 31 ± 6** | 32 ± 4 | 37 ± 5 |
| 100 mg/kg, 6 hr. fasted | 70 ± 13 | 42 ± 11 | 95 ± 19 | 42 ± 7** |
| 200 mg/kg, 6 hr. fasted | 76 ± 17 | 35 ± 7 | 51 ± 19 | 24 ± 3 |
| 200 mg/kg, ad lib fed | 56 ± 17 | 26 ± 3 | 29 ± 7 | 35 ± 12 |

*TI different from 0, paired-t test, p .05
**TI different from 0, paired-t test, p .01

As a result of the above tests it was found that TI decreased daily food intake by dose-dependently decreasing average meal size. The effect of TI on meal size was delayed since the size of the first meal after a 6-hour fast was not changed by TI in lean rats and was decreased by only one dose of TI (100 mg/kg) in obese rats, Table I. The interval to the second meal was decreased in lean rats by 100 and 200 mg/kg TI and in obese rats by 50, 100 and 200 mg/kg TI. The size of the second meal was decreased in lean rats by 100 mg/kg TI and in obese rats by 50 mg/kg TI and there were trends for decreased second meal size in response to other doses of TI. Thus, in 6-hour fasted rats, TI affected mainly the second meal, which was smaller and initiated sooner. In ad libitum fed rats 200 mg/kg TI increased the size of the first meal after administration in obese rats only, but did not affect the time interval until, or the size of, the second meal.

Daily feeding behaviors were analyzed for responses to TI in 3-hour increments using the feeding behavior apparatus described. As may be seen fron Table I, the lowest dose of TI (25 mg/kg) did not affect feeding behavior of obese or lean rats. In obese rats, 50 mg/kg TI decreased food intake starting 9 hours after treatment administration. While meal size was decreased starting 3 hours after treatment, a trend for an increase in number of meals resulted in no difference in cumulative intake until 9 hours when average meal size was decreased and number of meals was unaffected. In lean rats, effects on cumulative food intake were transient; overall average meal size was larger and the number of meals was fewer in response to 50 mg/kg TI.

The dose of 100 mg/kg TI decreased cumulative food intake starting 12 hours after administration in both obese and lean rats. In obese rats, average meal size was decreased for all time periods, but cumulative food intake was not affected until 12 hours because meal frequency was increased the first 9 hours. In lean rats there was a trend for decreased meal size for all time periods and, as for obese rats, the affect on cumulative food intake was delayed because of initial increases in meal frequency.

Cumulative food intake was decreased by 200 mg/kg TI from 3 and 6 hours after administration in obese and lean rats respectively. For all time periods meal size was decreased significantly in obese rats and non-significantly in lean rats. Meal frequency was not affected.

In ad libitum fed rats 200 mg/kg TI decreased food intake was about the same as in 6-hour fasted rats, but meal patterns were affected differently. In obese rats average meal size was increased the first 3 hours, but decreased after 12 hours. In lean rats only 18 hour cumulative food intake was decreased, but there were trends for decreased cumulative food intake and average meal size beginning 9 hours after treatment.

Water intakes were measured during these experiments and were significantly decreased in 6-hour fasted rats by 100 mg/kg TI in obese rates (30±4 vs. 43±2 ml, $p<0.05$) and by 200 mg/kg TI in both obese (24±2 vs. 37±1, $p<0.01$) and lean rats (25±2 vs 32±1 ml., $p<0.05$). In ad libitum fed rats 200 mg/kg TI also decreased water intake (26±3 vs. 35±1 ml, $p<0.01$ in obese rats and 22±3 vs. 30±1 ml., $p<0.05$ in lean rats).

Thus, a single dose of TI decreased daily food intake by decreasing average meal size in a dose-dependent manner in both obese and lean rats.

Experiment II. Food Intake and Body Weight Responses to Administration of TI for 7 Days Eight obese and eight lean female Zucker rats were individually housed in a room maintained at constant temperature (24° C.) and 12-hour light-dark cycle. They were offered Purina rat chow pellets and water ad libitum. During Weeks 1 through 5, daily body weights and food and water intakes were recorded. During Week 2, four of the obese rats and their lean mates were administered 2.0 mg/kg water intragestically twice a day. The other four obese and four lean rats were administered 100 mg TI/kg in 2.0 ml/kg water intragastrically twice a day. During Week 4, the treatments were reversed for each rat. To measure body weight responses, changes from the beginning of the treatment were analyzed. To measure food and water intake responses, cumulative changes from the average of the pretreatment weeks were calculated. These changes in response to TI and control treatments were analyzed using paired-t tests. To compare recoveries from each treatment period, changes from the preliminary weeks were calculated and analyzed using paired-t tests.

As a result of the chronic experiments, it was found that the administration of 100 mg/kg TI twice daily decreased body weight gain and daily food intake in obese rats. The greatest difference in body weight gain was on Day 3, with the difference not increasing during subsequent days of treatment. By Day 9 (two days after treatment was terminated) the change from the pretreatment period in body weight after TI was not different from that after control. Food intake also was decreased most on Day 3. Average food intake remained decreased after TI compared with control treatments for two days after treatment was terminated. Change in water intake in obese rats was less after TI than after control treatments for Day 1 ($-3\pm1$ vs. $-5\pm1$ ml, $p<0.05$). In lean rats administration of TI for 7 days did not significantly affect body weight gain; change in daily food intake was less after TI than control treatment only on the first day.

In summary, these experiments show that a trypsin inhibitor, when administered to 6-hour fasted rats, decreased daily food intake by decreasing meal size in both obese and lean rats; and, when administered daily for one week, decreased food intake and daily weight gain in obese rats. Thus, it is reasonable to conclude that the trypsin inhibitor is responsible for the decreased weight in rats because of decreased food intake rather than because of the decreased digestion of protein.

The smaller and less consistent effects of TI on feeding behavior of lean compared with obese rats and the lack of response of lean rats to 7-day administration of TI may be due to the amount of TI administered per animal. Obese rats received 30 to 60 percent more TI on a per animal basis because the amount given was on a per kg weight basis. Since the site of action of the TI may be intraluminal, the concentration in the intestine of obese rats may have been higher than that in lean animals, although the weight of the small intestine is greater in obese rats than lean rats ($8.5\pm0.7$ vs. $6.6\pm5$ g, $t=3.09$, $p<0.02$) based on unpublished data. However, even when the response of lean and obese to similar amounts of TI per animal were compared, those of lean rats were smaller and less consistent.

There is evidence that decreased food intake in response to TI is due to increased secretion of CCK because, it is postulated, TI inhibits the negative feedback signal for CCK secretion. Thus, increased food intake responsivity of obese rats to TI may be due to a larger increase in secretion of CCK on obese compared with lean rats. However, obese rats are less sensitive than lean rats to the effects of exogenously administered CCK on food intake, pancreas growth and pancreatic exocrine function. They are also less sensitive than lean rats to the effects of the TI used in these experiments on pancreas growth. Thus, while the effect of TI on food intake may be related to secretion of CCK, the increased sensitivity of obese rats relative to lean rats to TI may be related to CCK secretion alone.

It is possible that, since different portions of the CCK molecule appear to be responsible for its principal actions, Zucker obese rats respond differently than lean rats to specific portions of the molecule. It has been shown by others that while CCK-4 is more potent than CCK-8 or CCK-33 in stimulating the endocrine pancreas, CCK-33 is more potent than CCK-8 or CCK-4 in stimulating amylase secretion from the pancreas. While CCK-8 represents 80% or more of the CCK-like immunoreactivity in the brain, it is reported to represent 50 percent of activity in small intestine with CCK-12 and smaller fragments representing the remainder. However, using a slightly different procedure, others have measured no CCK-33 or CCK-8 in extracted duodenum; only CCK-22 was present. The proportions of the circulating forms might possibly differ between lean and obese rats. Thus, differing sensitivities of Zucker rats to different effects of CCK could be due to differences in the structural form of CCK present, or in the case of the trypsin inhibitor, the different form of CCK released from the duodenum.

These same tests have shown in 18-hour fasted rats that administration of a purified soybean trypsin inhibitor decreased duodenal content of CCK-22 by half by 20 minutes, and by 60 minutes the content had returned to pretreatment levels. They also showed that at 30 and 60 minutes intestinal amylase increased five-fold and pancreatic amylase decreased by half. If, in the rats used in the present tests, the same events were occurring at approximately the same times, then the rats, which were allowed to eat 15 minutes after being administered TI, would have about one-half the duodenal CCK content released at that time. Thus, CCK concentration should be greater than after control treatment and might affect the first meal. While the first meal was not affected by most treatments, postmeal interval was significantly decreased, perhaps due to increased motility and transit rate in the duodenum caused by presence of more CCK. Also there were trends for decreased size of the second meal. Thus, the effect of the trypsin inhibitor appeared to be delayed even though duodenal content of CCK may have been decreased 50 percent within 20 minutes of administration of TI.

One can only speculate why in obese rats 200 mg/kg TI decreased first meal size after a 6-hour fast and increased first meal size after no fast. It is possible that when no food was initially present in the duodenum the TI could fully inhibit the trypsin feedback signal, but when food was present the action of the TI itself was inhibited, thus decreasing secretion of CCK. This immediate increase in food intake in ad libitum fed rats was followed by decreased food intake because six hours later food intake after TI was the same as that after control.

Although it is possible that decreased food intake during the first few hours after TI may be due to increased CCK release because of inhibition of the trypsin negative feedback signal, decreased food intake during subsequent hours may not be a direct effect of increased CCK concentration. Several reaons for this delayed effect may be postulated. The first is that since most of the CCK in the gastrointestinal tract is found in the proximal one-third of the duodenum, in several hours the bolus of TI administered would have moved beyond this part of the intestine. However, it has been shown that TI can affect pancreatic secretion for as long as six hours after administration. The second reason resides in the fact that as long as 60 minutes after administration of TI, intestinal amylase was increased. The increased amylase and possibly other pancreatic enzymes in the short-term may have increased the digestion and absorption of nutrients. The increased availability of nutrients may have decreased the energy requirement thereby decreasing food intake. The third possibility is that since the decreased cumulative intake in response to TI occurs primarily in the dark portion of the diurnal cycle, hormonal or behavioral changes occurring then may have a significant influence on the observed responses.

When rats were administered TI twice daily for 7 days, only the obese responded, and the decreased body weight was accompanied by decreased food intake. Thus, the decreased body weight demonstrated in raw soybean meal-fed rats and attributed to trypsin inhibitors, may have been due to decreased food intake because of increased section of CCK, although decreased digestion of the food is a possible reason for weight loss. Lack of effect of TI on body weight in lean rats is consistent with results of other studies with TI in normal weight rats. That obese rats responded might have been due to increased dosage per rat or possibly the form of CCK released. The effect of TI on food intake and body weight lasted for several days after the last treatment was administered; thus, TI could have a long-term effect which might be used to produce weight loss in obese subjects. Results of these experiments have demonstrated that the decrease in body weight caused by TI administration may be due to decreased food intake and meal size, which may be a response to increased secretion of CCK from the duodenum.

Evidence for trypsin as a negative feedback signal for CCK secretion was obtained using rats in which pancreatic juice was diverted from the intestine (17). In these rats administration of trypsin decreased secretion of protein from the pancreas, indicating that CCK secretion was decreased.

In conducting the experiments reported in Table I, trypsin inhibitor available under the tradename FOY was used. Another commercially available form of trypsin inhibitor known as TRASYLOL, available through Mobay Chemical Corp., New York, NY, was used in another set of tests, the results of which were shown to replicate the results of the test employing FOY, and substantiated the conclusion previously established; namely, that by administering a controlled amount of a synthetic trypsin inhibitor, there results a dose-dependently decrease in meal size and a decreased body weight over time. The results of the tests employing TRASYLOL are recorded in Table II, which follows:

TABLE II

Feeding behavior of six-hour fasted Zucker obese and lean rats (n = 8 pairs) in response to intragastric administration of TRASYLOL.

| | First Meal Size (g) | Postmeal Interval (min) | Second Meal Size (g) | Daily Food Intake (g) |
|---|---|---|---|---|
| Obese | | | | |
| Water | 6.53 | 184 | 3.60 | 32.18 |
| Trasylol | 3.60 | 117 | 2.16 | 31.41 |
| Lean | | | | |
| Water | 4.01 | 168 | 1.62 | 26.24 |

TABLE II-continued

Feeding behavior of six-hour fasted Zucker obese and lean rats (n = 8 pairs) in response to intragastric administration of TRASYLOL.

| | First Meal Size (g) | Postmeal Interval (min) | Second Meal Size (g) | Daily Food Intake (g) |
|---|---|---|---|---|
| Trasylol | 2.12 | 138 | 1.71 | 25.74 |

TRAYSLOL EXPERIMENT: Materials and Methods

In the tests involving the administration of TRASYLOL, eight obese (597±25) and eight normal-weight (435±20) male Zucker rats were individually housed in Plexiglass cages (Lafayette Instrument Company) in a room maintained at constant temperature (20° C.) and 12-hr light-dark cycle. The rats were trained, using a continuous reinforcement schedule, to press a bar to obtain each food pellet (45 mg, Noyes Company, Inc.). Each bar press was recorded on a counter and on a magnetic tape (Kennedy, 800 bit per inch) with a time base using a data acquisition system (Massey-Dickinson). Subsequently a Sperry Univac V77 computer was used to store data from the magnetic tape and to determine meal patterns. The criteria for a meal were a minimum of 10 presses in a minimum of 10 min with a minimum intermeal interval of 10 min. Water was available ad libitum. Food was available ad libitum except on experimental days when access to the bar and feeder cup was denied for 6-hr starting at "lights-on". Fifteen min. before rats were allowed access to the bar and feeder cup, they were administered control or treatment solutions via a gastric tube. Food then was available for at least 42 hours before the next treatment day. The size and duration of the first meal after the fast, the length of the interval to the second meal, the second meal size, and the number of presses for food 18 hours after treatment were recorded. For each test series 18 hr meal patterns were analyzed for one dose of each compond. Each obese rat was paired with a lean rat, and treatments were assigned to pairs of rats.

The trypsin inhibitor TRASYLOL was intragastrically administered at the dose of 121,000 KIU/kg, which is approximately equal to 100 mg. of the trypsin inhibitor FOY. Because of the volume of TRASYLOL required (12.1 ml/kg), one-half was administered 45 minutes and one-half 15 minutes before access to food was allowed. Meal patterns were analyzed after control and TRASYLOL treatments.

The results realized in the tests conducted using TRASYLOL have been summarized in Table II from whence it is apparent that the administration of TRASYLOL decreased the sizes of the first meal, which were larger in obese relative to lean rats. Postmeal intervals were not affected by the treatment. Second-meal sizes were larger in obese rather than lean rats, but overall were not affected by treatment. However, by orthogonal comparisons, second-meal sizes were decreased in obese rats but not in lean rats. Daily food intakes, while larger in obese rats relative to lean rats, were not affected by treatment.

An analysis of feeding behavior in three-hour intervals showed that overall cumulative food intakes were not affected by the administration of the TRASYLOL. Average meal sizes were decreased by TRASYLOL, and such decreases were larger in obese rats relative to lean rats. The number of meals taken were increased through the administration of TRASYLOL compared to the number of meals taken by rats being administered control, and such increase in numbers was more in obese rats rather than lean rats and further increased with the time interval.

In the test conducted with TRASYLOL, it was found that when administered 15 minutes before feeding, there was a resultant decrease in the size of the first meal after the six-hour fast in both obese and lean rats, but the feeding behavior of the obese rats was affected for a longer period than that of the lean rats since the size of the second meal was smaller in obese relative to lean rats. In addition, in obese rats, average daily meal size was decreased more than in lean rats after treatment with TRASYLOL. Thus, both TRASYLOL and FOY were found to decrease food intake, primarily by decreasing average meal size and, in obese rats, the responses were stronger and more lasting.

The fact that the same results obtained through the administration of controlled quantities of two diverse trypsin inhibitors supports the conclusion that all trypsin inhibitors, when so administered, will have the same affect on food intake. This conclusion is further substantiated by reason of the fact that the two synthetic trypsin inhibitors tested have quite diverse chemical structures and physical characteristics. TRASYLOL has a relatively large molecular size making it incapable of being absorbed into the intestines while FOY is smaller and is readily absorbed. The molecular weight of FOY is approximately 500, while that of TRASYLOL is approximately 6,000.

The results set forth above concerning the controlled administration of effective amounts of the trypsin inhibitors FOY and TRASYLOL support the conclusion that all trypsin inhibitors will have the same effect on food intake. It is also probable that the naturally occurring tryspin inhibitors to be found in products other than soybeans, including lima beans, chicken egg white and extracts of beef pancreases, when properly administered will result in a decrease in food intake.

Although the specification defines the results of controlled experiments conducted on rats alone, the same results may be expected when controlled amounts of trypsin inhibitors are administered to other mammals, including humans. While other synthetic trypsin inhibitors may be available, their identity is unknown at this time; nevertheless, based on the foregoing results, it is expected that any newly developed synthetic trypsin inhibitors will produce similar results. Accordingly, any modification, variation or equivalent steps and/or constituents within the scope of the appended claim should be considered to be within the scope of the invention.

Having described in detail my invention, I claim:

1. A method of stimulating satiety in mammals by administering to them a therapeutically effective amount of a trypsin inhibitor which stimulates the release of cholecystokinin.

2. The method defined in claim 1 wherein the trypsin inhibitor is orally administered.

* * * * *